United States Patent [19]

Kang

[11] 3,945,944

[45] Mar. 23, 1976

[54] CATALYST FOR THE PRODUCTION OF HYDROGEN AND/OR METHANE

[76] Inventor: Chia-Chen Chu Kang, 301 Gallup Road, Princeton, N.J. 08540

[22] Filed: Feb. 8, 1974

[21] Appl. No.: 440,824

Related U.S. Application Data

[63] Continuation-in-part of Ser. No. 203,847, Dec. 1, 1971, abandoned.

[52] U.S. Cl............ 252/455 R; 252/459; 252/466 J; 252/473; 48/197 R
[51] Int. Cl.$^2$...................... B01J 29/06; B01J 29/10
[58] Field of Search............ 252/459, 455 R, 466 J, 252/473; 48/197 R

[56] References Cited
UNITED STATES PATENTS

| | | | |
|---|---|---|---|
| 3,432,443 | 3/1969 | Davies et al. | 252/459 |
| 3,650,713 | 3/1972 | Chinchen et al. | 252/459 X |

*Primary Examiner*—Carl F. Dees

[57] ABSTRACT

A cobalt promoted nickel catalyst supported on refractory material and a process employing said catalyst for the production of hydrogen-containing gases, such as synthesis gas, reducing gas or town's gas, or for the production of methane-enriched gases, such as pipe-line gas.

5 Claims, 1 Drawing Figure

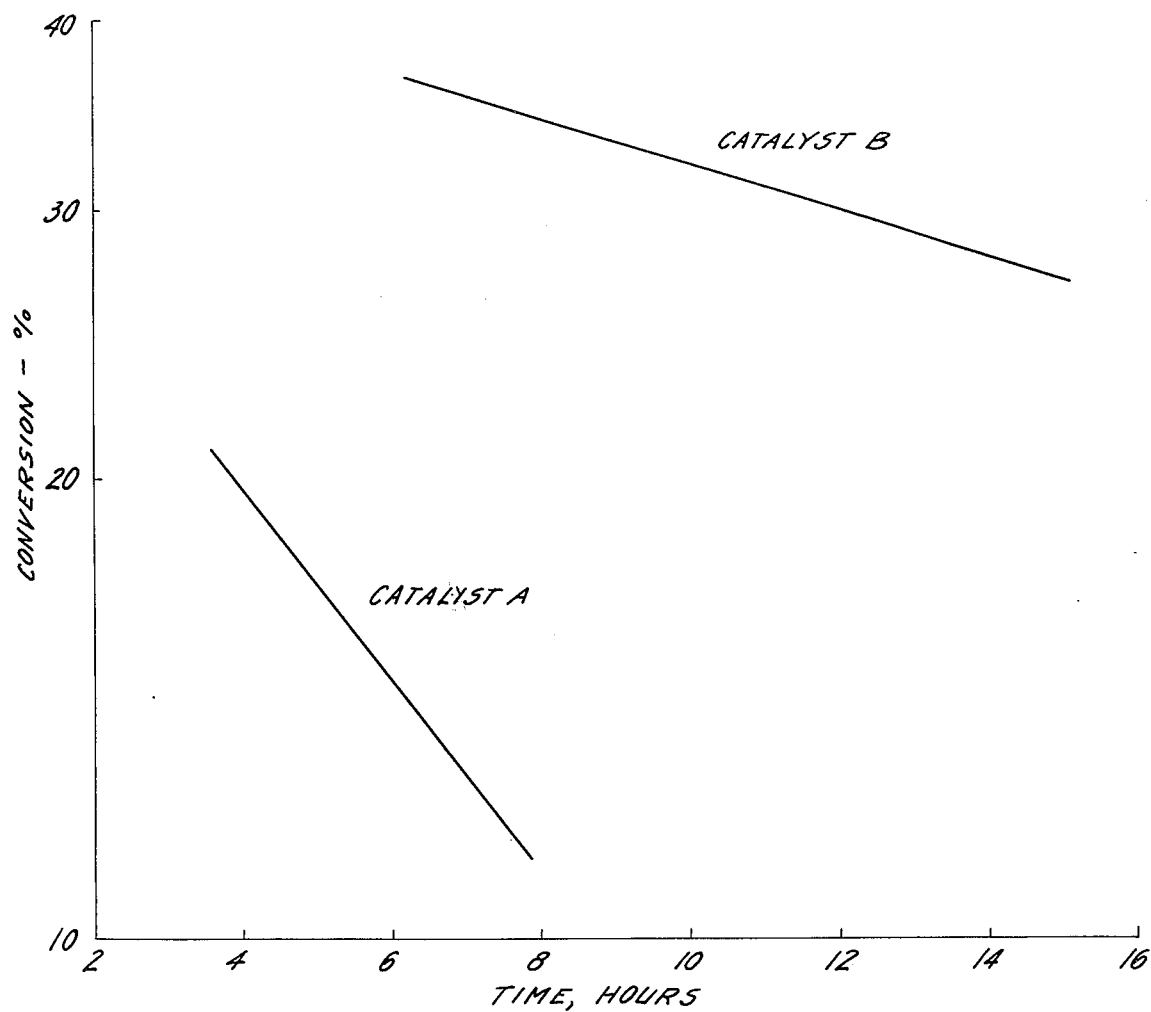

CATALYST FOR THE PRODUCTION OF HYDROGEN AND/OR METHANE

This application is a continuation-in-part of pending application Ser. No. 203,847, filed Dec. 1, 1971, now abandoned.

In the production of hydrogen and methane-containing gases by steam reforming of hydrocarbon feeds a catalyst comprised of nickel on a refractory support is generally used commercially. When methane is the feed material, there is a certain tendency of carbon being deposited on the catalyst, and when reforming feedstocks containing higher paraffins and/or unsaturated hydrocarbons such as olefins and aromatics, such a deposition of carbon takes place more markedly. The deposition of carbon deactivates the catalyst and/or disintegrates the catalyst and moreover causes an undesirable pressure drop in the reactor. As a result the unit must frequently be shutdown in order to steam off the carbon, and in case of severe carbon deposition the catalyst must be replaced. One method for minimizing the deposition of carbon is to use a considerable excess of steam, but this procedure renders the process more expensive. The prior art, e.g. British Pat. No. 1,182,829, has also suggested the alternate use of catalyst comprised of cobalt on refractory support for the steam-reforming of hydrocarbons, the cobalt catalyst being taken as equivalent in performance to the above-mentioned nickel catalyst. To provide a method for operating at economically feasible levels of steam, a nickel or cobalt catalyst promoted with an alkali compound, such as a potassium compound, can be used, e.g., of the type disclosed in British Patent No. 1,095,997 or in U.S. Pat. No. 3,417,029. However, under relatively high operating temperatures alkali-promoted catalysts suffer loss of the alkali through vaporization. Not only does such a loss cause the catalyst to lose its ability to reduce carbon deposition, but also it causes the alkali to be deposited in equipment downstream of the reactor such as in heat exchangers or waste heat boilers, resulting in severe fouling of the equipment and in loss of heat exchange efficiency. U.S. Pat. No. 3,432,443 discloses a method for increasing the porosity and activity of a cobalt-containing steam-reforming catalyst by subjecting it to a lengthy heat treatment at temperatures above 600°C (1112°F) in a non-reducing atmosphere prior to reduction. However, such heat treatment is shown not to reduce the tendency of carbon laydown and in order to enable trouble-free operations under steam-reforming conditions the catalyst must be promoted with alkali, which limits its use to relativelymild operating conditions for the reasons discussed above. The patent also discloses that a lengthy heat treatment of a nickel containing catalyst at temperatures above 600°C rarely if ever increases activity. Another catalyst for operation at relatively low steam-to-carbon ratios, disclosed in U.S. Pat. No. 3,385,670 is a cobalt catalyst on a zirconia support, which has a surface area of less than one square meter per gram. This catalyst has a disadvantage in that zirconia is a rather expensive supporting material. The same disadvantage is had with the nickel-zirconia or cobalt-zirconia catalyst disclosed in U.S. Pat. No. 3,650,713.

It is, therefore, an object of the present invention to provide a new and improved catalyst for the production of hydrogen-rich or methane-rich gases, which catalyst is capable of providing operation at relatively low steam-to-carbon ratios without deleterious carbon deposition on the catalyst, has a long life at high operating temperatures and is economical to manufacture.

Another object of this invention is to provide an improved catalyst which is active at low operating temperatures.

Another object is to provide an improved catalyst for the conversion of feeds selected from methyl fuel or a hydrocarbon mixture comprising paraffins, naphthenes, olefins and aromatics to a hydrogen or methane-rich product gas at steam requirements which are significantly lower than those required by employing a standard catalyst.

Still another object is to provide a catalyst and process for the production of methane-enriched gas, such as pipeline gas.

A further object of this invention is to provide a process for the production of hydrogen-containing gaseous product, such as synthesis gas, reducing gas or town's gas employing the said catalyst.

Various other objects and advantages of this invention will become apparent from the accompanying description and disclosure.

According to this invention, a new and improved catalyst is provided, which comprises a member of the group consisting of elemental cobalt, a reducible compound of cobalt and mixtures thereof, a member of the group consisting of elemental nickel, a reducible compound of nickel and mixtures thereof, and a refractory material comprised of at least one member taken from the group consisting of oxides of aluminum, silicon, magnesium, calcium, titanium and compounds thereof, said catalyst being substantially free of alkali. The cobalt content of this catalyst should be at least about 0.5 weight percent calculated as the metal, preferably between about 2 and about 20 weight percent. The nickel content can range from about 5 to about 70 weight percent calculated as the metal, preferably between about 15 and about 60 weight percent. In all cases the ranges above refer to the respective contents after calcination of the catalyst at 1000°F.

The remainder of the catalyst is comprised of a refractory support containing one or more of the oxides of aluminum, calcium, silicon, magnesium or titanium or compounds thereof. It can also contain a naturally occurring material, such as kaolin or bauxite. The preferred refractory support is aluminum oxide or a mixture of aluminum oxide and calcium oxide. The surface area of the refractory should be at least one square meter per gram and preferably lie in the range from about 20 to about 200 square meters per gram. A lubricating or binding agent such as graphite or stearic acid may be included to facilitate the forming of catalyst powder into desired shapes.

The catalyst of the invention can be prepared in a number of ways. One method of preparation is by impregnating a high surface area refractory support with a solution of cobalt and nickel salts, such as nitrates, which salts upon subsequent heat treatment at temperatures of 1100°F and below will decompose to the corresponding oxides. After impregnation, the composite is dried at temperatures at about 250°F. and above and heat treated at a temperature of 1100°F and below under substantially non-reducing conditions, preferably in the range from about 800°F to 1050°F. The high surface area of a refractory support is usually decreased by severe heat treatment, hence it is essential to maintain the heat treatment at the aforementioned relatively low temperature level. An alternate impregnation technique is to impregnate a commercial nickel containing high surface area catalyst with a solution of cobalt salt followed by the above-mentioned drying and heat treatment. Another method of preparation is the coprecipitation technique, which is generally conducted by mixing together aqueous alkaline solutions of one or more of the compounds including aluminate, silicate and titanate, and aqueous acid solutions of nickel and cobalt and, if desired, of other acid-soluble compounds such as calcium or magnesium. When the acidic salt solution is mixed with the alkali solution, all the components are precipitated as their hydroxides, provided that there is sufficient alkali to neutralize the acid salt solution. A small excess of alkali is desirable to ensure complete precipitation. The precipitate is filtered, washed substantially free of alkali and heat treated in one or more steps at temperatures from about 250°F to 1100°F under substantially non-reducing conditions. This heating drives off the water, converts the hydroxides to oxides, and produces mainly hydraulic bonds. A modification of the coprecipitation technique is to add a cobalt and nickel salt solution to an aqueous slurry of the supporting material, then sufficient amount of alkali, such as sodium or potassium hydroxide or carbonate, is added to precipitate the cobalt and nickel in hydroxide or carbonate form, both of which are converted to the corresponding oxides upon heating. The catalyst may also be prepared by mixing the components in the form of fine powders without departing from the scope of this invention. Regardless of the manner of producing the catalyst, the cobalt portion thereof is never subjected to heat treatment above 1100°F in a non-reducing atmosphere prior to reduction.

The catalyst can be shaped into a variety of common shapes and sizes, such as cylindrical rings or pellets of various sizes.

Prior to use, the catalyst can subsequently be subjected to a reduction treatment at elevated temperatures, e.g., at the process temperature, in the presence of a reducing medium such as hydrogen or a mixture of hydrogen and steam. This treatment is conveniently carried out in the reactor prior to the introduction of feed thereto. In the case of steam reforming of a feed containing predominatly methane the catalyst can be reduced during the reforming operation and the separate reduction step is omitted.

Heretofore it has been understood by skilled workers in the art that in the reforming of hydrocarbons with steam and/or other oxygen containing gases, nickel is equivalent to cobalt in carbon deposition characteristics. The present invention teaches that a catalyst containing a combination of cobalt and nickel supported on high surface area refractory material gives superior and synergistic performance in minimizing carbon deposition. The specific advantages of the catalyst of the invention is that the catalyst simultaneously exhibits the following qualities: 1) it has a long life, i.e., it maintains acceptable activity for a long period of time, 2) it is active at low temperatures such as at 600°F and below, 3) it is capable of operations at low steam-to-carbon ratios without imposing limitations on maximum operating temperature, and 4) it is inexpensive to produce.

In accordance with the present invention there is also provided a process for the production of gaseous products taken from the group consisting of hydrogen-rich and methane-rich gases, which comprises contacting a member of the group consisting of hydrogen, methyl fuel and hydrocarbon and mixtures thereof with an oxygen-containing gas taken from the group consisting of steam, air, oxygen, oxides of carbon and mixtures thereof over a catalyst which comprises a member of the group consisting of elemental cobalt, a reducible compound of cobalt and mixtures thereof, a member of the group consisting of elemental nickel, a reducible compound of nickel and mixtures thereof, and a refractory material comprised of at least one member taken from the group consisting of oxides of aluminum, silicon, magnesium, calcium, titanium and compounds thereof, said catalyst being substantially free of alkali. Particular applications of the process is in the steam reforming of one or more hydrocarbons to hydrogen or methane-rich gases and in the methanation of hydrogen and carbon oxides-containing gases to produce methane-enriched gas.

The process of this invention can be carried out over a wide range of operating conditions including temperatures between about 400° and about 2200°F., pressures from about 0 to about 1500 psig. and steam-to-carbon ratios from about 0 to about 5.0. The levels of these conditions are dictated by the desired product gas composition and the equilibrium gas composition as well as the temperature and pressure levels of any subsequent process step and the overall economics of the process. Generally, for the production of hydrogen-rich gas, the operation is carried out at high temperature and low to medium pressure, whereas for the production of methane-rich gas the process is effected at low temperature and relatively high pressure.

In carrying out the process of the invention the oxygen-containing gas can be taken from the group consisting of steam, air, oxygen, oxides of carbon and mixtures thereof. In the case of steam reforming of a hydrocarbon feed steam and/or carbon dioxide can be used, with steam being the preferred gas. However, other members of the above-mentioned group can be used for certain specific applications of the steam-reforming, for example, a mixture of steam and air is used when the product is an ammonia synthesis gas. In the case of methanation the oxygen-containing gas is a carbon oxide, usually a mixture of carbon monoxide and carbon dioxide, which is reacted with hydrogen feed to form methane.

The catalytic steam reforming process of this invention is applicable to methyl fuel and a great variety of hydrocarbon feedstocks including paraffins, naphthenes, olefins and aromatics, said feeds ranging from one to forty carbon atoms per molecule. The hydrocarbon feedstocks can be a single hydrocarbon such as methane, ethane, ethylene, propane, propylene, butane, etc., or mixtures thereof including natural gas and its condensate, petroleum refinery and petrochemical streams such as refinery gases, by-products from ethylene plants, etc., and various petroleum fractions such as light naphtha, heavy naphtha, gas oil, etc. The term "methyl fuel" is defined as crude methanol made from natural gas to facilitate shipping.

For the steam reforming process of the present invention, the relative amount of steam and hydrocarbon reactants is expressed as the steam-to-carbon ratio, which is the number of moles steam per atom of carbon in the hydrocarbon charged to the reactor. For example, a reactor charge of six moles of steam per mole of ethane corresponds to a steam-to-carbon ratio of 3.0. Minimum steam-to-carbon ratio is the ratio below which the rate of carbon deposition is sufficiently rapid to cause a significant rise in pressure drop across the catalyst bed. To those skilled in the art, it is known that the minimum steam-to-carbon ratio varies with the hydrocarbon feed. Among paraffins, olefins and aromatics having the same number of carbon atoms, the minimum steam-to-carbon ratio increases with increasing degree of unsaturation in the hydrocarbon, i.e., paraffins need the lowest ratio and aromatics the highest ratio. Within the same group of hydrocarbons the minimum steam-to-carbon ratio increases with increasing molecular weight. The steam-to-carbon ratio required to provide a reasonable period of carbon-free operation in a commercial unit is usually higher than the minimum steam to carbon ratio. For economical and reaction-equilibrium considerations the steam-to-carbon ratio is preferred to be about 5.0 or less.

In order to put the variety of hydrocarbon feeds on the same space velocity basis, the space velocity is expressed herein as standard volume of $C_1$ hydrocarbon equivalent fed per hour per volume of catalyst. For example, when feeding two gram moles of hexane per hour over one liter of catalyst the equivalent $C_1$ space velocity is (2) (6) (22.4) = 268.8 lit./hr./lit. Space velocity in the catalytic reforming process of this invention ranges broadly between about 100 and about 20,000 v/hr./v.

A detailed discussion is given below covering the preferred steam reforming conditions for three commercial gas products, namely, reducing gas, synthesis and town's gas.

In the production of reducing gas used, for example, in the direct reduction of iron ore, it is necessary for economic reasons to keep the steam-to-carbon ratio extremely low in order to produce a gas product, which does not require drying prior to its introduction to the reducing zone. Generally, the reducing gas should contain at least 88 mole percent of hydrogen and carbon monoxide on a wet basis. The process is carried out at the high end of the temperature range and low end of the pressure range, for example, at reactor outlet temperatures of between about 1800°F and about 2200°F and at pressures from about 0 to about 150 psig. The steam-to-carbon ratio ranges from about 1.0 to about 1.3 and the $C_1$ equivalent space velocity is maintained between about 100 to about 2000 v/hr/v. The feed to the process is usually a low molecular weight hydrocarbon such as natural gas. The catalyst of this invention is particularly useful in producing this type of reducing gas because of its capability to function well at extremely low steam-to-carbon ratios, i.e., close to stoichiometric requirements, without encountering carbon deposition.

When employing the catalyst of the invention to produce synthesis gas for the manufacture of ammonia or methanol, a variety of hydrocarbon feeds can be used ranging from normally gaseous feeds such as natural gas to normally liquid feeds such as naphtha or higher boiling petroleum fractions. The preferred operaring conditions include reactor outlet temperatures between about 1300°F and about 1800°F, pressures from about 50 to about 1000 psig., steam-to-carbon ratios in the range between about 1.5 and about 5.0 and $C_1$ equivalent space velocity generally up to about 4000 v/hr/v. With heavier feedstocks the space velocity is maintained at relatively low values while with lighter feeds it is possible to operate at higher values. For instance, space velocities of 3000 and higher can be employed when reforming natural gas over the catalyst of the invention.

When the catalyst of the present invention is employed to convert hydrocarbons other than methane to methane-rich town-3 s gas with moderately high heating value such as about 500 B.T.U. per standard cubic foot (high heating value), the conditions are preferably maintained at about 700° to about 1200°F, between about 300 to about 800 psig, from about 1.0 to about 5.0 steam-to-carbon ratio and at a high space velocity, such as between about 1000 and about 20,000 $C_1$ equivalent velocity.

The production of methane-enriched gas such as pipeline gas containing about 90 mole percent of methane or more can be carried out by first producing a methane-rich gas under conditions suitable for town's gas production, followed by a methanation reaction promoted by the catalyst of the invention to convert hydrogen and carbon oxides produced in the first reaction into methane. Water and carbon dioxide are subsequently removed from the methanation product. In the methanation reaction two major reactions occur:

$$CO + 3H_2 \rightleftharpoons CH_4 + H_2O$$

$$CO_2 + 4H_2 \rightleftharpoons CH_4 + 2H_2O$$

Both reactions are exothermic and are favored by low temperature. Although the overall reaction is favored by low partial pressure of steam, it is not necessary to remove steam from the feed to the methanation zone, i.e., the effluent from the reforming zone. Since the reforming reaction is endothermic and the methanation reaction is exothermic and the latter is favored by a lower temperature than the former, it is advantageous to effect the process in two or more stages, which may be contained in a single vessel or a multiple of vessels. The multiple stage system possesses the advantage in that external means can be provided for cooling between stages resulting in high thermal efficiency of the process. Since water is one of the products of the methanation reactions, water can be removed between stages so as to drive the reactions towards completion. An almost pure methane product can be produced after removal of carbon dioxide by conventional means. The methanation step is preferably carried out between about 400° and about 800°F, from about 300 to about 800 psig, from about 1000 to about 10,000 $C_1$ equivalent space velocity and at steam-to-carbon ratios from about 0 to about 1.5. For the methanation step steam-to-carbon ratio and $C_1$ equivalent space velocity are based on the total carbon atoms including carbon oxides present in the feed.

It is to be understood that the scope of the present invention as it pertains to the production of methane-enriched gas also includes the methanation of hydrogen and carbon oxide-containing gaseous mixtures other than reformer effluents. Also, the carbon dioxide removal step may be omitted, if desired.

The following examples are offered to illustrate the present invention:

CATALYST A

This catalyst is a commercial steam reforming catalyst, Chemetron Corporation G-56B, having the following analysis on a weight basis after calcination at 1000°F: 1.9% nickel oxide which corresponds to 25% nickel metal, 60.5% $Al_2O_3$, .% CaO, 0.15% $SiO_2$ and 0.22% $Fe_2O_3$. G-56B is further characterized by having a surface area of 58 square meters per gram. After crushing and sizing the catalyst to 12 to 20 mesh, it is designated as Catalyst A.

CATALYST B

A 500 gram aliquot of Catalyst A is impregnated with a solution of cobalt nitrate in an amount sufficient to yield 5 weight percent cobalt calculated as the metal in the catalyst. The solution is prepared by dissolving 129.6 grams of cobaltous nitrate hexahydrate in 150 cc. of distilled water. The impregnated mixture is mixed thoroughly, dried at 250°F, then calcined at 1000°F for 2 hours.

CATALYST C

A 100 gram aliquot of Catalyst A is impregnated with a solution of sodium carbonate in an amount sufficient to yield 3.5 weight percent sodium calculated as the metal in the catalyst. The solution is prepared by dissolving 8.4 grams of sodium carbonate in 60 cc. of distilled water. The impregnated mixture is mixed thoroughly, dried at 250°F, then calcined at 1,000° for 2 hours.

Experiments are made in a tubular reactor fitted with an internal thermowell. The reactor, which is heated in an electrical furnace, is connected with an instrument for measuring the pressure drop across the catalyst bed. The catalyst is charged to the reactor and a layer of Alundum chips is placed above the catalyst to serve as a preheating zone. Water is metered though a calibrated flow meter and vaporized. The gaseous feed is metered separately, preheated and mixed with steam at the reactor inlet. In the experiment with liquid feedstock, the feed is metered, then mixed and vaporized together with the water and introduced to the reactor. When reduction with hydrogen is carried out, the hydrogen is metered, preheated and admitted to the reactor. After 2 hours the hydrogen flow is stopped, and the feed and steam are introduced. During operation the catalyst temperature is measured, and the pressure drop across the catalyst bed is monitored in the experiments conducted at atmospheric pressure to give an indication whether or not carbon is forming and plugging the bed. The product gas is cooled to remove the unreacted water and any liquid hydrocarbon. The cooled product gas is measured and a sample is taken for analysis.

EXPERIMENTS 1, 2 and 3

These comparative experiments are conducted employing a laboratory test designed for evaluating the carbon deposition characteristics of the steam reforming catalyst. The minimum steam-to-carbon ratios of Catalyst A, Catalyst B and Catalyst C are determined under synthesis gas operating conditions. The feed in all three experiments is a 1:1 mixture of ethylene and ethane on a volume basis. The operating temperature, pressure space velocity are kept at the same levels in these three experiments, while the steam-to-carbon ratios are gradually decreased during experimentation. The operating conditions are set forth in Table I. The commercial Catalyst A shows tendencies of severe carbon laydown at a steam-to-carbon ratio of 4.0 as indicated by the pressure drop increase of 2 inches $H_2O$/hr., and thus the minimum steam-to-carbon ratio is 4.0. Catalyst B, a cobalt promoted nickel catalyst, however, does not show an increase in pressure drop across the catalyst bed at a steam-to-carbon ratio of 1.5 reached at the end of the experiment, and Catalyst B thus has a minimum steam-to-carbon ratio of less than 1.5. The advantage of the cobalt promoter of the invention in greatly improving the carbon deposition characteristic of the nickel catalyst is clearly demonstrated.

Catalyst C, an alkali-promoted nickel catalyst, does not show any increase in pressure drop across the catalyst bed at a steam-to-carbon ratio of 1.5. Experiments 2 and 3 indicate that the cobalt promoter is as effective as the alkali promoter, which has been recognized for its efficiency in minimizing the deposition of carbon on the catalyst.

EXPERIMENT 4

In this experiment methane is fed to the reactor, which is maintained at conditions suitable to produce a reducing gas, and which is charged with Catalyst B. The operating conditions and results are shown in Table I. Operation at extremely low steam-to-carbon ratio of 1.2 is possible with the catalyst of the invention to produce a reducing gas containing 95.3 mole percent (wet basis) of hydrogen and carbon monoxide.

TABLE I

| PRODUCTION OF HYDROGEN-RICH GAS | | | | |
|---|---|---|---|---|
| EXPERIMENT NO. | 1 | 2 | 3 | 4 |
| Catalyst Designation | A | B | C | D |
| Added Promoter, wt. % | 0 | 5% Co | 3.5% Na | 5%Co |
| Feed | ethylene: ethane | ethylene: ethane | ethylene: ethane | methane |
| Operating Conditions: | | | | |
| Catalyst Volume, cc. | 25 | 25 | 25 | 25 |
| Hydrogen Reduction | No | No | No | No |
| Reactor Outlet Temperature, °F. | 1400 | 1400 | 1400 | 1850 |
| Reactor Pressure, psig. | 0 | 0 | 0 | 0 |
| Space velocity cc. $C_1$ equiv./hr./cc. Cat. | 120 | 120 | 120 | 500 |
| Steam-to-carbon ratio | 4.0 | 1.5 | 1.5 | 1.2 |
| Pressure drop increase, inches $H_2O$/hr. | 2 | 0 | 0 | 0 |
| Product Gas Analysis, mole % | | | | |
| $H_2$ | 73.4 | 70.5 | 72.0 | 71.8 |
| CO | 12.9 | 25.2 | 23.6 | 23.5 |
| $CO_2$ | 13.7 | 4.3 | 4.4 | 0.3 |
| $CH_4$ | 0 | 0 | 0 | 0 |
| $C_2$ | 0 | 0 | 0 | 0 |

TABLE I-continued

| PRODUCTION OF HYDROGEN-RICH GAS | | | | |
|---|---|---|---|---|
| EXPERIMENT NO. | 1 | 2 | 3 | 4 |
| Catalyst Designation | A | B | C | D |
| Added Promoter, wt. % | 0 | 5% Co | 3.5% Na | 5%Co |
| Feed | ethylene: ethane | ethylene: ethane | ethylene: ethane | methane |
| Operating Conditions: | | | | |
| $H_2O$ | /1/ | /1/ | /1/ | 4.4 |

/1/Gas composition reported on dry basis.

EXPERIMENT 5

The suitability of the catalyst of the invention for production of town's gas is demonstrated by this example, the operating conditions and results being shown in Table II. A light naphtha feed having an end point of about 300°F. and containing on the average 6 carbon atoms per molecule of naphtha is treated over Catalyst B under conditions suitable to produce town's gas. The product gas has a heating value of 631 BTU/SCF on a dry basis.

EXPERIMENT 6

This experiment is carried out to demonstrate the excellent capability of the catalyst of the invention as an active methanation catalyst under the relatively low temperature conditions required for the reaction. The feed in this experiment is mixed to simulate the composition of the wet product gas from Experiment 5, i.e., a gas mixture is first prepared having the composition of the dry product gas in Table II and to this mixture steam is added in a proportion of 0.75 moles steam per mole of dry gas. The operating conditions and results are shown in Table II. An excellent pipeline gas is produced having a heating value of 741 BTU/SCF including $CO_2$. After $CO_2$ removal the heating value is 964 BTU/SCF.

TABLE II

| PRODUCTION OF METHANE-RICH GAS | | |
|---|---|---|
| Experiment No. | 5 | 6 |
| Catalyst Designation | B | B |
| Added Cobalt, wt. % Co | 5 | 5 |
| Feed | Light Naphtha | Reformer Effluent |
| Operating Conditions: | | |
| Catalyst Volume, cc. | 25 | 25 |
| Hydrogen Reduction, °F | 1000 | 600 |
| Reactor Outlet Temp. °F. | 1000 | 600 |
| Reactor Pressure, psig. | 400 | 400 |
| Space Velocity, cc. $C_1$ equiv./hr./cc.Cat | 1000 | 1000 |
| Steam-to-carbon ratio | 1.5 | 0.93 |
| Product Gas Analysis, mole% (dry basis) | | |
| $H_2$ | 19.3 | 3.5 |
| CO | 0.8 | trace |
| $CO_2$ | 22.9 | 23.1 |
| $CH_4$ | 57.0 | 73.4 |
| $C_2$ and higher | 0 | 0 |
| BTU/SCF including $CO_2$ | 631 | 741 |
| BTU/SCF excluding $CO_2$ | | 964 |

EXPERIMENT 7 and 8

These two comparative experiments are carried out with Catalysts A and B employing conditions which are similar to those of Experiment 5, designed for the production of town's gas. However, a very high space velocity is used in these experiments to effect an incomplete conversion of the feed in order to enable comparisons of catalyst activity and stability within short periods of time. The operating conditions are maintained at the same levels in both Experiments, which use n-hexane as feed. At intervals, samples are taken of the product gas and analyzed and each experiment is allowed to proceed until a definite change in conversion is observed. The conversion of n-hexane is calculated from the carbon balance, i.e. it is 100 times the ratio of the number of carbon atoms in the product gas to the number of carbon atoms in the n-hexane charged to the reactor. The data are summarized in Table III and the pertinent results are graphed in FIG. 1. As shown, the addition of cobalt to a nickel catalyst dramatically decreases the rate of catalyst deactivation, hence a much longer catalyst life is expected.

TABLE III

| DEACTIVATION OF STEAM REFORMING CATALYST | | | | |
|---|---|---|---|---|
| Experiment No. | 7 | | 8 | |
| Catalyst Designation | A | | B | |
| Added Cobalt, wt. % Co | 0 | | 5 | |
| Feed | n-hexane | | n-hexane | |
| Operating Conditions | | | | |
| Catalyst Volume, cc. | 3 | | 3 | |
| Hydrogen Reduction, °F | 932 | | 932 | |
| Reactor Outlet Temp. °F | 932 | | 932 | |
| Reactor Pressure, psig. | 294 | | 294 | |
| Space Velocity cc. $C_1$ equiv./hr./cc/ Cat. | 20000 | | 20000 | |
| Steam-to-carbon ratio | 5.0 | | 5.0 | |
| % Conversion versus operating Time | Hour | % Conv. | Hour | % Conv. |
| | 4.5 | 18.3 | 8.1 | 31.8 |
| | 5.5 | 15.7 | 10.1 | 35.6 |
| | 6.5 | 13.7 | 12.1 | 29.9 |
| | | | 13.1 | 29.3 |
| | | | 15.1 | 26.8 |

What is claimed is:

1. A substantially alkali-free, heat treated catalyst composition for the production of gases rich in hydrogen or methane with decreased carbon lay-down prepared by a method which comprises:

supporting on a refractory material having a surface area of at least one square meter per gram and selected from oxides of aluminum, silicon, magnesium, calcium, titanium or mixtures thereof a. between about 5 and about 70 weight percent basis the total catalyst weight and calculated as the metal of a nickel compound selected from elemental nickel, a reducible compound of nickel or mixtures thereof;

b. at least 0.5 weight percent basis the total catalyst weight and calculated as the metal of a cobalt compound selected from elemental cobalt, a reducible compound of cobalt or mixtures thereof;

after support of the cobalt compound on the refractory, heat treating the catalyst composition under non-reducing conditions at a temperature of at most 1100°F.

2. The catalyst composition of claim 1, in which the heat treatment is carried out at a temperature in the range from about 800°F to about 1050°F.

3. The catalyst composition of claim 1, in which the surface area of the refractory material ranges between about 20 and about 200 square meters per gram.

4. The catalyst composition of claim 1 which the cobalt content of the catalyst is between about 2 and about 20 weight percent calculated as the metal.

5. The catalyst composition of claim 1 in which the nickel content of the catalyst is between about 15 and about 60 weight percent calculated as the metal.

* * * * *